United States Patent
Eaton et al.

(10) Patent No.: US 8,334,768 B2
(45) Date of Patent: Dec. 18, 2012

(54) SYSTEMS AND METHODS FOR DETERMINING A LOCATION OF A MEDICAL DEVICE

(75) Inventors: Scott Eaton, Briarcliff Manor, NY (US); James Fidacaro, Mountain Lakes, NJ (US); Jack Balji, Mahwah, NJ (US)

(73) Assignee: Mindray DS USA, Inc., Mahwah, NJ (US)

( * ) Notice: Subject to any disclaimer, the term of this patent is extended or adjusted under 35 U.S.C. 154(b) by 528 days.

(21) Appl. No.: 12/645,327

(22) Filed: Dec. 22, 2009

(65) Prior Publication Data

US 2011/0148624 A1    Jun. 23, 2011

(51) Int. Cl.
*G08B 1/08* (2006.01)
*G08B 13/14* (2006.01)

(52) U.S. Cl. ......... 340/539.13; 340/539.11; 340/539.12; 340/572.1

(58) Field of Classification Search ............... 340/573.1, 340/573.11, 573.12, 539.13, 572.1, 572.8, 340/10.1; 235/375, 385; 700/2, 216; 705/3; 604/890.1; 455/41.2, 41.3
See application file for complete search history.

(56) References Cited

U.S. PATENT DOCUMENTS

| | | | |
|---|---|---|---|
| 5,265,594 A | 11/1993 | Olsson et al. | |
| 6,658,118 B1 | 12/2003 | Kumar et al. | |
| 7,941,096 B2 * | 5/2011 | Perkins et al. | 455/41.2 |
| 7,997,474 B2 * | 8/2011 | Zuhars et al. | 235/375 |
| 8,040,238 B2 * | 10/2011 | Perkins | 340/539.13 |
| 8,089,354 B2 * | 1/2012 | Perkins | 340/539.13 |
| 2007/0233035 A1 * | 10/2007 | Wehba et al. | 604/500 |
| 2007/0233520 A1 * | 10/2007 | Wehba et al. | 705/3 |
| 2007/0233521 A1 * | 10/2007 | Wehba et al. | 705/3 |
| 2007/0267940 A1 | 11/2007 | Wright | |
| 2009/0120439 A1 | 5/2009 | Goebel | |
| 2010/0090004 A1 * | 4/2010 | Sands et al. | 235/385 |
| 2010/0121156 A1 * | 5/2010 | Yoo | 600/300 |

FOREIGN PATENT DOCUMENTS

EP    2116752 A1    11/2009

* cited by examiner

*Primary Examiner* — Van T. Trieu

(74) *Attorney, Agent, or Firm* — Kory D. Christensen; Stoel Rives LLP

(57) ABSTRACT

Medical devices to be located on a network include a unique identifier, which may be transmitted to a server over the network. The network may have a plurality of network connection points. The server may include a location subsystem configured to store a location of each of the plurality of network connection points. The server may also include a device tracking subsystem configured to store a last known device location based on the unique device identifier. The last known location of the medical device may be updated when the medical device is connected to the network based on the location of the one of the plurality of network connection points used to transmit the unique device identifier.

29 Claims, 5 Drawing Sheets

FIG. 2

Device Tracking Module
118

| ID or MAC Address 201 | Device Type 202 | Calibration Date 203 | Owner Information 204 | Expiration Information 205 | Diagnostic Information 206 | Last Known Location 207 | Date Last Used 208 |
|---|---|---|---|---|---|---|---|
| 00:01:AE:02:45:21 | Patient Monitor | 1-Dec-2010 | Cardiology | N/A | Voltage 10V+/- 2V | Room A12 Cardiology | In Use |
| 2 | Sensor Module | 1-Dec-2009 | Cardiology | 1-Dec-2010 | Voltage 5V+/- 2V | Room A12 Cardiology | In Use |
| 3 | ECG Sensor | 1-Dec-2009 | Cardiology | 1-Dec-2010 | Voltage 5V+/- 1V | Room A12 Cardiology | In Use |
| 4 | $CO_2$ Sensor | 31-Aug-2009 | Emergency Room | 1-Dec-2009 | Voltage 5V+/- 1V | Room A10 Cardiology | In Use |
| 00:02:32:AC:21:89 | Docking Station | 1-Jun-2010 | Emergency Room | 1-Dec-2009 | Voltage 10V+/- 2V | Room E1 Emergency | 23-Aug-2009 |
| ... | ... | ... | ... | ... | ... | ... | ... |

200

SYSTEMS AND METHODS FOR DETERMINING A LOCATION OF A MEDICAL DEVICE

TECHNICAL FIELD

The present disclosure relates to systems and methods for determining a location of a medical device having a unique identifier on a network.

BRIEF DESCRIPTION OF THE DRAWINGS

FIG. 2 illustrates one exemplary data structure for a device tracking module.

DETAILED DESCRIPTION OF PREFERRED EMBODIMENTS

Figure 1:
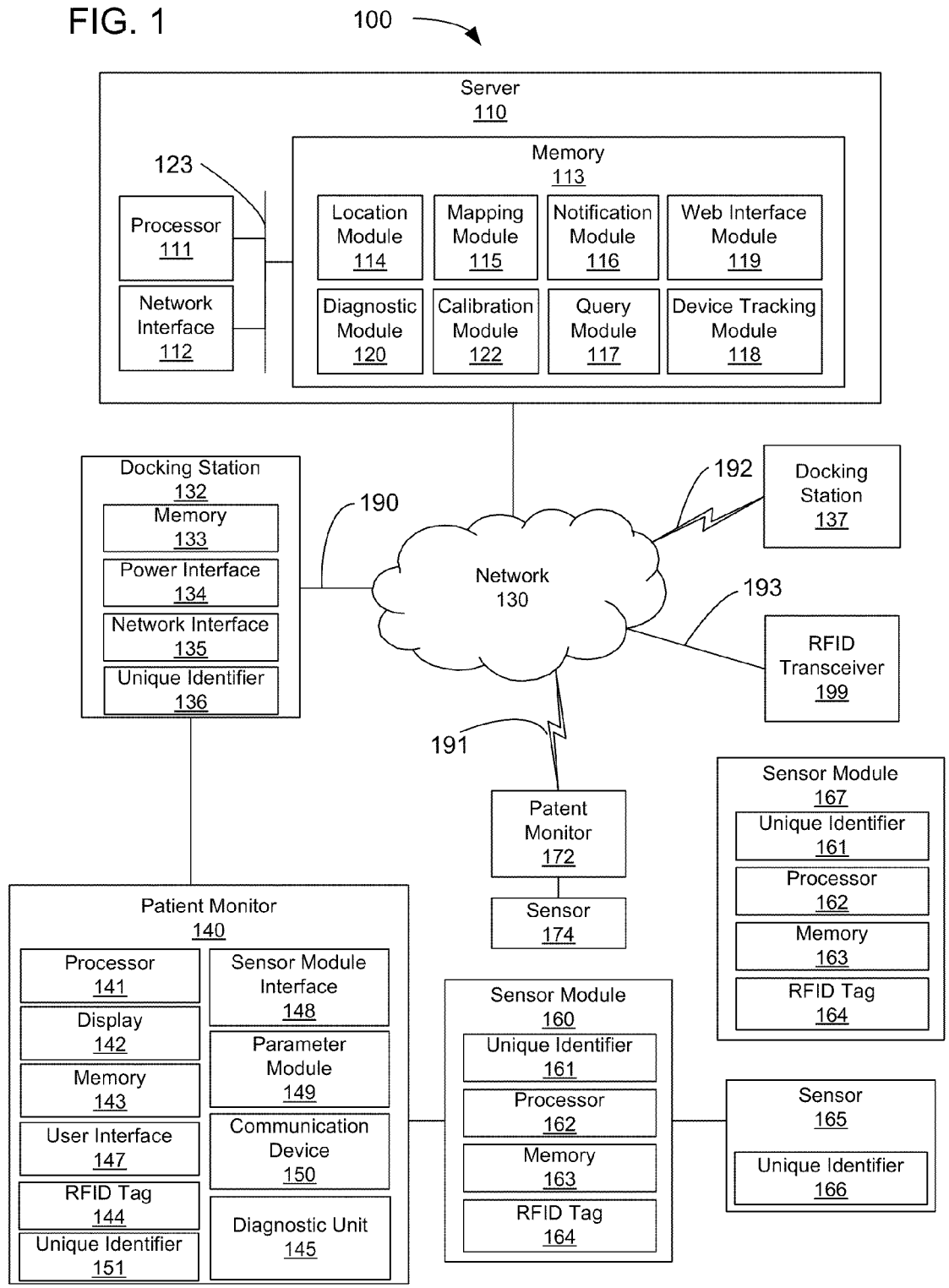
FIG. 1 illustrates a simplified functional block diagram of one embodiment of a system for determining the location of a medical device.

A variety of types of equipment may be utilized in hospitals and other medical facilities to acquire, analyze, and display data from sensors attached to a patient. The data may include, for example, pulse, temperature, respiration, blood pressure, blood oxygen, electrocardiogram, and other patient parameters. It is often desirable to continuously monitor patient parameters when transporting patients. When a patient is moved (e.g., the patient is transferred from one hospital ward to another), patient monitoring equipment may also be transported.

Tracking of patient monitoring equipment and other types of medical equipment within a medical facility can pose difficulties. As mobility of patient monitoring systems and other devices is enhanced, and as greater functionality is included within devices, this problem is compounded. For example, an electrocardiogram (ECG) sensor may be attached to a patient who enters a hospital at an emergency room. The ECG sensor may be attached to a module that is configured to receive measured information from the sensor and translate the information into an electronic representation. The module may in turn be connected to a patient monitor, which may display the information collected by the sensor. As a patient moves throughout a hospital, the patient monitor and related equipment may travel with the patient. For example, the patient may travel to a radiology ward and a cardiology ward before being discharged. If the patient is discharged from the cardiology ward, the patient monitor and related equipment, which may have initially been located in the emergency room, may now be located in the cardiology ward. The foregoing example illustrates only one of many possible scenarios in which equipment is moved from one location to another in a hospital. Further, the task of locating a particular piece of equipment (e.g., to perform required maintenance or calibration), even if the general location of the equipment is known (e.g., the equipment remains in a particular ward in a hospital), may be time consuming.

For these and other reasons, it may be desirable to track the location of a variety of types of equipment. A tracking system may help to ensure that equipment is properly accounted for (e.g., to ensure that equipment does not go missing), is properly configured, and is properly utilized. The practice of manually tracking the movement of equipment and implementing processes to ensure that equipment is returned to a particular ward in a hospital or other medical facility may be inefficient and cumbersome. The systems and methods disclosed herein may be employed to track the location of equipment that is connectable to a network, to identify equipment that requires calibration, to identify equipment that is expired, and/or to identify equipment that is malfunctioning.

In one embodiment, the systems and methods disclosed herein may be employed in connection with a wide variety of medical devices that are connectable to an electronic network. For example, in a hospital, a variety of patient monitors, modules, cables, and sensors may be connected in various ways to an electronic network. Each device to be tracked may include a unique device identifier, which may be transmitted to a server via a device identification subsystem when the device is connected to the network. Using the unique device identifier and a system for determining the location of each of a plurality of network connection points, the location of each device may be tracked as the medical device interacts with the network. In alternative embodiments, such systems may also include other functionality configured to ensure that the medical device has not expired, to determine when a medical device requires calibration, or when a medical device should be returned to some other location.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or detailed description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform the processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of computer-readable media suitable for storing electronic instructions.

FIG. 1 illustrates a simplified functional block diagram of one embodiment of a system 100 for determining the location of a medical device in a hospital or other medical facility. In the illustrated embodiment, system 100 may be configured for tracking docking stations 132, 137, patient monitors 140, 172, sensor modules 160, 167, and sensor 165. In other embodiments, the locations of other types of devices, or a plurality of types of devices, may also be tracked. For example, cables for patient monitoring, as described in co-pending U.S. patent application Ser. No. 12/432,558, which is incorporated herein by reference, could be tracked. Each piece of equipment to be tracked is associated with a unique identifier 136, 151, 161, 166, that identifies each piece of equipment within system 100.

System 100 includes a plurality of network connections 190, 191, 192, 193. In the exemplary embodiment shown in FIG. 1, network connections 190, 191, 192, 193 may each be associated with a particular location (e.g., a particular room in a hospital, a particular area, such as a supply closet, etc.). System 100 includes a plurality of docking stations 132, 137 connected to respective network connections 190, 192. The location of docking stations 132, 137 may be determined based on the location associated with the network connection to which each docking station is connected. For example, the locations of docking stations 132, 137 may correspond to a particular room or department within a hospital.

Patient monitors 140, 172 may be mobile, and may allow patients to be continuously monitored in transit without requiring that a patient be disconnected from a respective patient monitor 140, 172. Accordingly, in certain embodiments, the patient monitors 140, 172 may each be configured to selectively couple with and selectively decouple from any of a plurality of docking stations (e.g., 132, 137).

In the illustrated embodiment, patient monitor 140 is shown as being coupled to docking station 132. Docking station 132 provides patient monitor 140 with power and/or a connection to a network 130, such as a hospital's local area network (LAN) and/or the Internet. Docking station 132 is illustrated as including a power interface 134 and a network interface 135. Power interface 134 may be configured to convert an alternating current (AC) power signal to a direct current (DC) power signal and/or provide power signal conditioning for patient monitor 140. Network interface 135 may include, for example, an Ethernet communication controller to allow the coupled patient monitor 140 to communicate through network 130 through docking station 132. Network interface 134 may be associated with a media access control (MAC) address. In certain embodiments, the MAC address of network interface 135 may be the same as unique identifier 136. It is contemplated that other types of identifiers may be utilized, including but not limited to serial numbers or arbitrarily assigned identifiers.

In certain embodiments, docking station 132 may also include a memory device 133. The memory device 133 may include non-volatile random access memory (RAM) that provides addressable storage and may be used in certain embodiments to store configuration settings and/or other types of data. In addition, or in other embodiments, memory device 133 stores a unique identifier 136 associated with docking station 132.

The patient monitor 140, according to the exemplary embodiment illustrated in FIG. 1, includes a processor 141, a display device 142, a memory 143, a radio frequency identifier (RFID) tag 144, a user interface 147, a sensor module interface 148, a parameter module 149, a communication device 150, a unique identifier 151, and a diagnostic unit 145. Among other tasks, processor 141 is configured to process patient data signals received through sensor module interface 148 and to display the patient data signals (e.g., as waveforms and/or numerical readouts) on the display device 142. Sensor module interface 148 may be connected to a sensor module 160, which may in turn be connected to a sensor 165. Sensor module interface 148 may be configured to process the acquired patient data signals in cooperation with the processor 141.

Patient monitor 140 may store the patient data signals in memory 143 along with other data. For example, patient monitor 140 may store a default set of configuration settings in memory 143. In various embodiments, configuration settings may be adjusted based on a location of patient monitor 140. In one example, the configuration settings required for a patient monitor 140 in an emergency room may differ from the settings required for a patient monitor 140 in an operating room. The default set of configuration settings may be selected based on the location of patient monitor 140.

The communication device 150 may be configured to communicate with network 130 through the network interface 135 of the docking station 132. Communication device 150 may be embodied using a wide variety of wired and wireless communication technologies, such as Ethernet, 802.11x, Ultra-wide band, Bluetooth, Zigbee, and the like.

In certain embodiments, patient monitor 140 includes an RFID tag 144, which may be interrogated by RFID transceiver 199. RFID transceiver 199 may be connected to network 130 by way of a network connection 193. RFID tag 144 may contain an integrated circuit known as an RFID transponder, which is connected to a small coupling coil. RFID transceiver 199 contains a coupling coil, connected to suitable electronics. In operation, the coil of RFID tag 144 is brought near the coil of RFID transceiver 199. The coil of RFID transceiver 199 excites the coil within RFID tag 144. In response to this excitement by RFID transceiver 199, RFID tag 144 may emit a radio frequency signal, which may correspond to a digital data stream. The digital data stream may correspond to unique identifier 151. The emitted radio frequency signal may be received by RFID transceiver 199, and unique identifier 151 may be passed via network 130 to server 110. Various manufactures produce commercially available RFID devices that may embody RFID tag 144 and RFID transceiver 199.

In certain embodiments, an RFID tag may also be placed on sensor modules, sensors, and/or other types of equipment, to help locate equipment that may not be currently in use. For example, as illustrated in FIG. 1, sensor module 167 is not connected to network 130. If a user desired to locate sensor module 167, the user may employ RFID transceiver 199 to query RFID tag 164 of sensor module 167. In this way, the location of sensor module 167 may be determined. Through the use of RFID transceiver 199, RFID tag 164 may be selectively activated and wirelessly connected to network 130 even though sensor module 167 may not be in use.

In certain embodiments, patient monitor 140 may comprise a diagnostic unit 145. Diagnostic unit 145 may be configured to perform a self-diagnostic test on patient monitor 140, sensor module 160, and/or sensor 165. Diagnostic unit 145 may be configured, for example, to read various voltages within patient monitor 140 or to determine other conditions. The results of a self-diagnostic test may be evaluated by diagnostic unit 145, or the results of the self-diagnostic test may be forwarded to server 110 via network 130 for evaluation.

Sensor module 160 may be configured to selectively couple with and decouple from the patient monitor 140. The coupling between sensor module 160 and patient monitor 140 can be mechanical, electrical, optical, and/or of any other suitable variety. For example, the coupling can be for physical union, communication, and/or power transfer. Sensor module 160 may be configured to interface a particular type of sensor (e.g., a $CO_2$ sensor, an ECG sensor) with patient monitor 140. Sensor module 160 may include electronic components that translate the input of a particular type of sensor into a more generic electronic format that can be utilized by patient monitor 140. In this way patient monitor 140 may interface with a wide variety of sensors. Sensor module 160 may include a processor 162 and a memory 163. Processor 162 and memory 163 may allow sensor module 160 to process information received from sensor 165 and prepare the information for use by patient monitor 140. In certain embodiments, a patient monitor may not require a sensor module in order to connect to a sensor. As illustrated in FIG. 1, for example, patient monitor 172 is connected directly with sensor 174.

Sensor 165 may be configured to sense a variety of types of data, including a patient's pulse, temperature, respiration, blood pressure, blood oxygen, electrocardiogram, and other patient parameters. Sensor 165 may be selectively coupled with sensor module 160. In certain embodiments, the sensor 165 may include an RFID tag for remote identification and/or data communication.

When a medical device, such as patient monitor 140, is connected to network 130 via docking station 132, patient monitor 140 may transmit unique identifier 151 to server 110. The transmission of unique identifier 151 and subsequent identification of patient monitor 140 may be accomplished by a device identification subsystem. The device identification subsystem may comprise a network operable to transmit unique identifier 151 together with the necessary components in server 110 (e.g., a processor 111 and appropriate data structure stored in a memory 113) to associate unique identifier 151 with patient monitor 140.

Server 110 may be connected to network 130 via a network interface 112. Server 110 comprises processor 111 and memory 113. A data bus 123 may provide a communication link between processor 111 and memory 113. Processor 111 may operate using any number of processing rates, architectures, and may be implemented using a general purpose or application specific processor. Processor 111 may be configured to perform various algorithms and calculations described herein. Processor 111 may be embodied as a general purpose integrated circuit, an application specific integrated circuit, a field-programmable gate array, and other programmable logic devices. The illustrated modules (reference nos. 114, 115, 116, 118, 119, 120, and 122) are executable by the processor.

Memory 113 may be implemented using a variety of computer-readable storage media, including hard drives, RAM, solid-state memory devices, and other storage media suitable for storing electronic instructions and other data. Certain embodiments may be provided as a computer program product including a computer-readable storage medium having stored instructions thereon that may be used to program a computer (or other electronic device) to perform processes described herein.

Although the embodiment illustrated in FIG. 1 illustrates various software modules located in memory 113, it is contemplated that in other embodiments, the functions associated with the various software modules may be performed in other ways. For example, various subsystems may be employed that utilize application specific integrated circuits or other hardware implementations to perform the described functions. Embodiments employing a combination of both hardware and software configured to perform the functionality of the various modules are also contemplated. Further, the functions of various modules illustrated in FIG. 1 may be distributed throughout system 100. Alternate embodiments may also include additional servers, which may operate as a distributed architecture.

A location subsystem 114 may be configured to associate the location of a plurality of network connections (e.g., network connects 190, 191, 192, 193) within a facility. In an embodiment having a wired network connection, location subsystem 114 may be programmed with the location of each wired connection. For example, each room in a hospital may be wired with a network interface. The location of each network interface may be recorded, and when a medical device is connected, the location of the medical device may be determined based on the location of the network connection to which it is connected. A similar approach may be taken with regard to wireless technologies, such as IEEE 802.11, Bluetooth, Zigbee, and RFID. When a medical device connects to a wireless transceiver (e.g., docking station 137 connecting to network 130 via wireless connection 192, or patient monitor 172 connecting to network 130 via wireless connection 191), the location of the medical device may be approximated using the location of the wireless transceiver. Refinements to the approximation are also contemplated, including but not limited to triangulation using multiple wireless transceivers, determination of signal strength, and other techniques in order to more accurately determine a location of a medical device connected wirelessly to a network. In various embodiments, the function of storing a location of each of the plurality of network connection points may be performed by a location subsystem.

A mapping subsystem 115 may be configured to display a location of a particular device within a facility. Mapping subsystem 115 may store a representation of the facility in which system 100 is employed. The representation of the facility, together with the information contained in location subsystem 114 may be utilized to generate a graphical representation of a location of a medical device on a map. Displaying the location graphically on a map, may assist users in locating a desired device. In embodiments utilizing wireless networks, mapping subsystem 115 may be configured to display an estimate of the area in which a desired device is located.

A notification subsystem 116 may be configured to provide notification upon the occurrence of a specified condition. A variety of conditions may prompt a notification. In certain embodiments, the conditions that prompt a notification may be user-customizable. For example, notification subsystem 116 may provide notification when a particular piece of equipment assigned to a first area in a hospital is removed from the first are or used for a specified amount of time in a second area of the hospital. In this way users of the equipment may be made aware of the fact that the piece of equipment should be returned to the first area. Notification subsystem 116 may also provide notification based on other criteria, including a notification that a particular device requires calibration, or that a particular device has expired (exceeded its useful life). Notification subsystem 116 may provide notification in a variety of ways, including, but not limited to, displaying a message on display 142, playing an audible message, placing a telephone call with a pre-recorded message, and/or sending an email, SMS, instant message, page, or other electronic message to a specified recipient. In alternate embodiments, the function of generating a notification when a specified condition is satisfied may be performed by a notification subsystem.

Web interface subsystem 119 may be configured to allow access to information stored in memory 113 via a web interface. The web interface may allow for access to information stored in memory 113 via an internal network, or intranet, or may allow for access from a wide-area network, such as the Internet.

Diagnostic subsystem 120 may be configured to interact with devices in system 100 to ensure that the medical devices are operating according to specified conditions. For example, diagnostic unit 145 in patient monitor 140 may be able to perform self-diagnostic tests, or may perform diagnostic tests on sensor module 160 and/or sensor 165. The results of these diagnostic tests may be transmitted via network 130 to sever 110, where the results may be evaluated by diagnostic subsystem 120. In certain embodiments, such as the embodiment illustrated in FIG. 2, certain diagnostic criteria may be stored in device tracking subsystem 118. The results of the diagnostic tests may be compared against the values stored in device tracking subsystem 118. Diagnostic subsystem 120 may be configured to prompt a user to take action when conditions of a medical device fall outside of specified parameters. For example, a nurse may be prompted to check sensor 165 and/or sensor module 160 when voltage readings from the sensor are outside of a certain range. Diagnostic subsystem 120 may also be configured to track instances of malfunction in order to identify equipment that may perform unreliably.

Calibration subsystem 122 may be configured to interact with devices in system 100 to ensure that the medical devices are calibrated on an appropriate schedule. For example, sensor module 160 may require calibration after some amount of cumulative use (e.g., 100 hours). System 100 may be configured to track the time that sensor module 160 is in use, and provide a notification when sensor module 160 is due for calibration. In some embodiments, device tracking subsystem 118 may be configured to track the cumulative time a particular sensor module is used. In other embodiments, sensor module 160 may comprise a processor 162 and a memory 163. Processor 162 and memory 163 may be configured to determine an amount of time that sensor module 160 is in use and the requirements for calibration. When calibration is required, sensor module 160 may notify a user of the need for configuration. Alternatively, sensor module 160 may communicate the need for configuration to server 110, and notification subsystem 116 may alert a specified user of the need for calibration. In various embodiments, the function of associating a medical device with calibration information and evaluating when the medical device requires calibration based on the calibration information may be performed by a calibration subsystem.

Query subsystem 117 may be configured to allow a user to query devices attached to network 130 and identify devices that satisfy a specified criteria. For example, a user may enter a query to locate a $CO_2$ module. In response to the query, system 100 may transmit the query to devices connected to network 130 and display a result indicating the location of each $CO_2$ module and the status of each module (e.g. whether the module is in use or not in use). In other embodiments, query subsystem 117 may be configured to interact with device tracking subsystem 118, which may be configured to maintain the location and status of various devices. Query subsystem 117 may also be configured to identify devices that are not connected to network 130 at the time of the query and to display the last known location of such devices that satisfy the specified criteria. The function of querying devices connected to network 130 to determine which devices satisfy a specified criteria may be performed by a device querying subsystem.

Device tracking subsystem 118 may be a repository for a variety of information regarding various devices to be tracked by system 100. Device tracking subsystem 118 may be configured to track a variety of types of equipment and a variety of types of information about each piece of equipment. Device tracking subsystem 118 may be queried by other modules or components in system 100. In various embodiments, the function of storing a variety of information regarding various devices to be tracked may be performed by a device tracking subsystem.

FIG. 2 illustrates one exemplary data structure for device tracking subsystem 118. As illustrated in FIG. 2, table 200 includes an ID or MAC address column 201 to associate each piece of equipment with a MAC address or other device specific identifier. Other types of data tracked by device tracking subsystem 118 may include device type 202, a calibration date 203, owner information 204, expiration information 205, diagnostic information 206, a last known location 207, and a date last used 208. Each type of data may be collected and utilized to add features to system 100 (FIG. 1). For example, the calibration date 203 may be utilized to determine when a particular device requires calibration. When calibration is required, a user may receive a notification and may then perform the required calibration. Similarly, expiration information 205 may also be tracked, and may permit the identification of expired equipment. Owner information 204 may also be tracked. Tracking such information may be desirable when a particular piece of equipment may be transported to other areas in a facility. In certain embodiments, a notification may be issued when a piece of equipment is utilized outside of a designated area. Expiration information 205 may be tracked to indicate when a particular piece of equipment will expire. Diagnostic information 206 may include information regarding certain criteria that can be measured in order to ensure that a particular device is operating within a prescribed range. A last known location 207 may be useful in locating devices that are not currently in use. For example, if a user desires to locate a particular item, a search for that item may be expedited by initiating the search in the location where the item was last used. The last used 208 information may also be utilized to help locate items by indicating which items are currently in use, and how long it has been since an item has been used.

Figure 3:
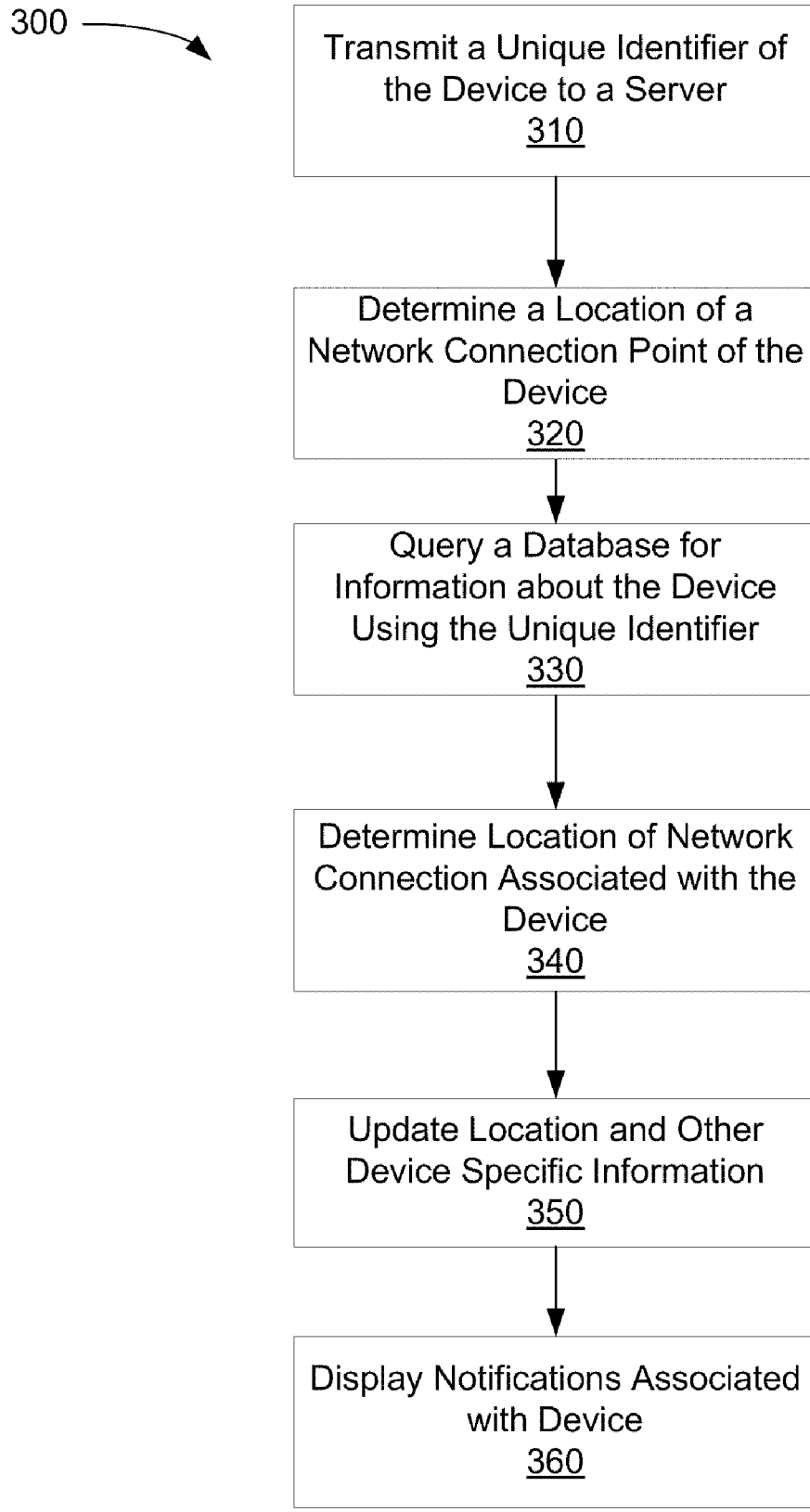
FIG. 3 illustrates a flow chart of one embodiment of a method for locating a medical device.

FIG. 3 illustrates a flow chart of one embodiment of a method 300 for locating a medical device. The medical device transmits 310 a unique identifier of the medical device to a server. Upon receipt of the unique identifier, the server may query 330 a device tracking subsystem for information using the unique identifier. The server may also determine 340 a location of the network connection associated with the medical device. The method 300 may then update 350 the location and other device specific information. In certain embodiments, the device specific information may include calibration information, expiration information, diagnostic information, the date the medical device was last used, and the like. If appropriate, any notifications associated with the medical device may be displayed 360.

Figure 4:
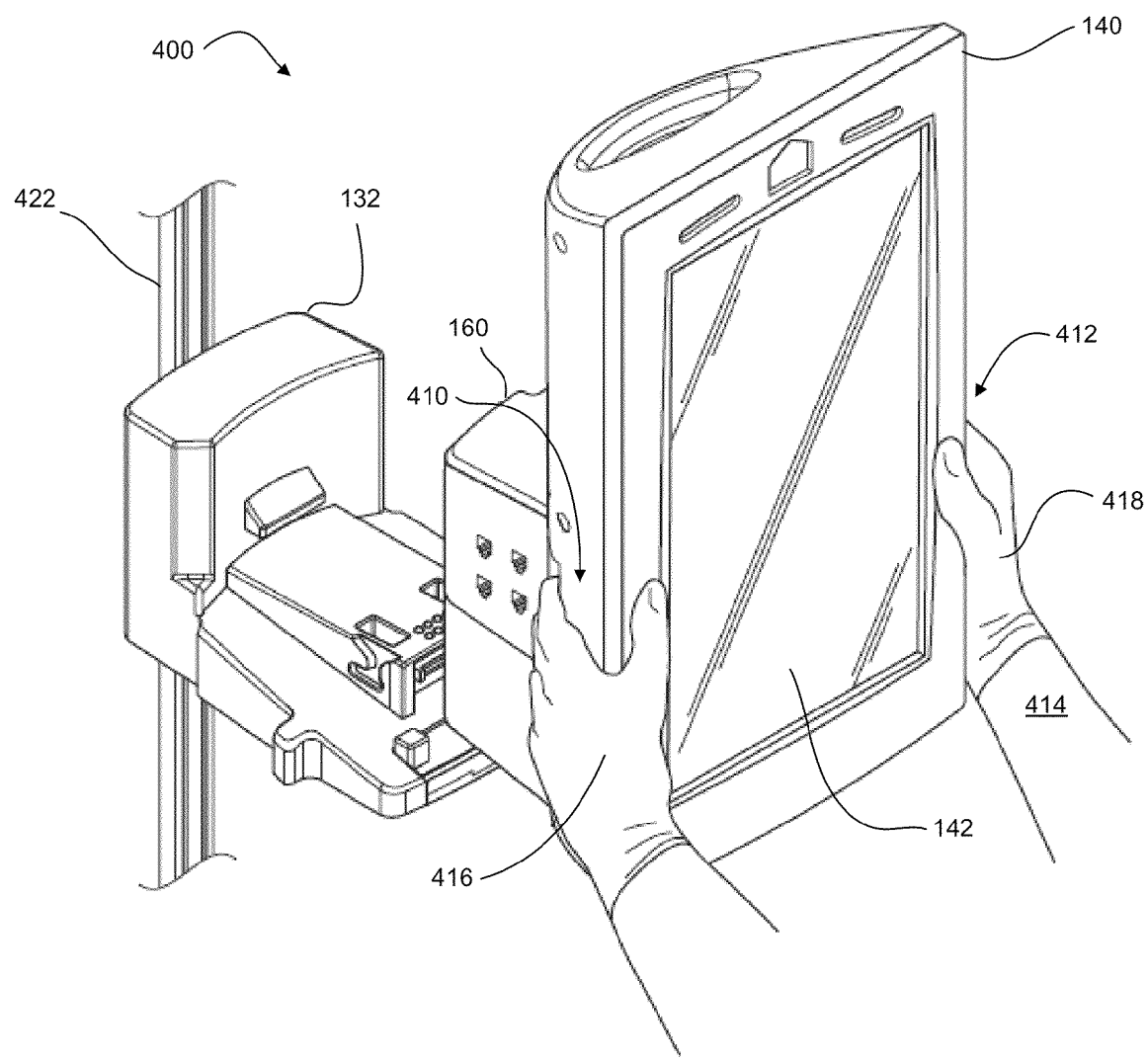
FIG. 4 is a front perspective view of a patient monitor according to one embodiment.

FIG. 4 is a perspective view of a patient monitor according to one embodiment. The embodiment shown in FIG. 4 is provided by way of example, and an artisan will understand from the disclosure herein that any portable patient monitoring system or other types of medical equipment may be used with the embodiments disclosed herein. System 400 includes a patient monitor 140, a sensor module 160, and a docking station 132. Patient monitor 140 can be configured to selectively couple with and decouple from docking station 132, and sensor module 160 can be configured to selectively couple with and decouple from patient monitor 140. Patient monitor 140 may include one or more gripping regions 410, 412 that are configured to aid in coupling and decoupling patient monitor 140 from docking station 132. For example, a medical practitioner 414 can firmly grasp with his or her hands 416, 418 gripping regions 410, 412 during removal of patient monitor 140 from docking station 132.

In FIG. 4, patient monitor 140 is illustrated as having been removed from docking station 132. A front surface of patient monitor 140 can include a display 142 that is configured to display information in a visually perceivable format. Screen 142 may be of any suitable variety, including those presently known and those yet to be devised. For example, screen 142 may include a liquid crystal display (LCD) panel. In some embodiments, screen 142 may be configured to receive information or otherwise interact with a medical practitioner. For example, screen 142 may include a touch screen.

Patient monitor 140 may include one or more ports for receiving or delivering information, which can include one or more serial ports, USB ports, Ethernet ports, DVI ports, or any other suitable variety of ports, interfaces, or connectors. In addition patient monitor 140 may include wireless connections (not illustrated), such as 802.11, UWB, Zigbee, Bluetooth, and the like. In some embodiments, information received via one or more of the ports can be displayed on the screen 142.

At least a portion of the information displayed by patient monitor 140 may represent information received from a patient or that otherwise relates to a patient. For example, in some embodiments, one or more sensors (not shown) are connected to the patient to sense a particular parameter, and information obtained via the one or more sensors is delivered to the sensor module 160. The sensors may deliver information to sensor module 160 via one or more cables (not shown) connected to one or more ports.

Sensor module 160 may be configured to process the information it receives from a sensor and deliver it to patient monitor 140, which can display the processed information. In some embodiments, patient monitor 140 may further process the information prior to displaying it. Patient monitor 140 may also display information that is independent of the patient, such as, for example, a notification regarding the configuration of patient monitor 140, or the need to calibrate sensor module 160.

Docking station 132 may be mounted in a substantially fixed position. For example, docking station 132 may be fixedly mounted to a wall within a hospital room in a single position by one or more plates, brackets, screws, bolts, or other mounting hardware and attachment devices. As another example, docking station 132 may be configured to transition among multiple fixed positions. For example, in the illustrated embodiment, docking station 132 is coupled to a mounting strip 422, which is in turn mounted to a wall (not shown) of a hospital room. Docking station 132 is capable of being adjusted upwardly or downwardly along a path constrained by one or more channels defined by mounting strip 422 so as to transition among a variety of positions. In each such position, docking station 132 can be fixed relative to mounting strip 422. In some embodiments, docking station 132 is coupled with mounting strip 422 via a mounting plate or a mounting bracket (not shown), the position of which can be adjusted upwardly or downwardly within the channels in any suitable manner.

Figure 5B:
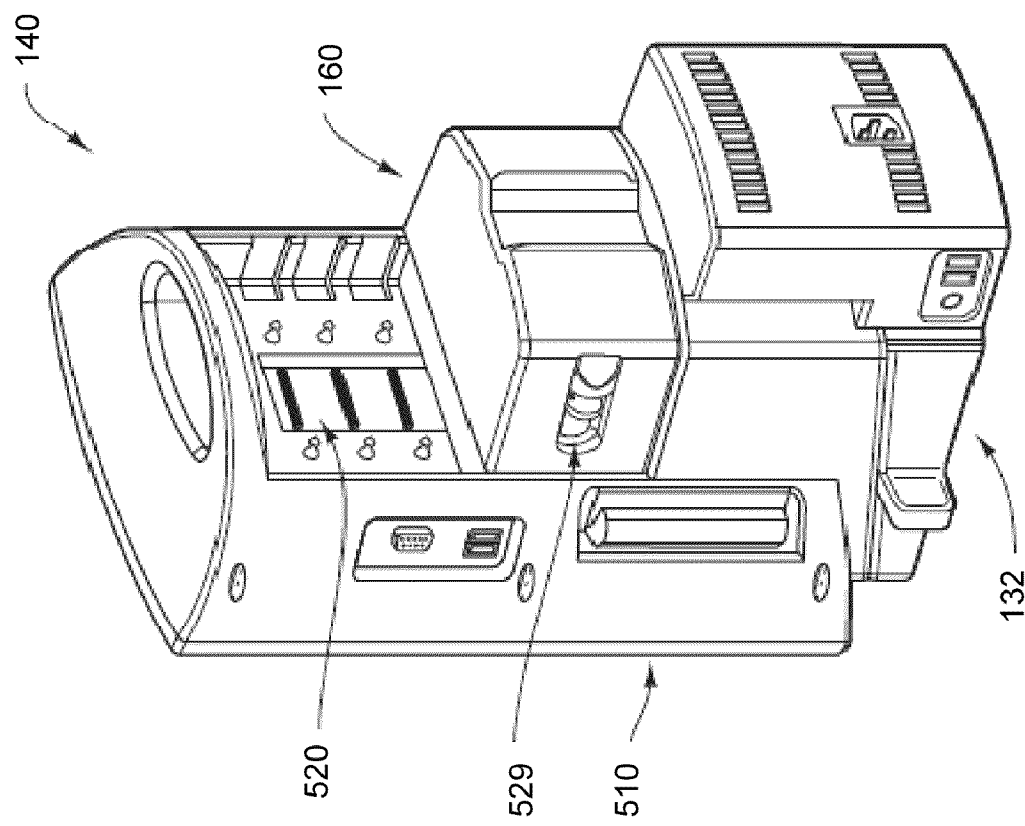
FIG. 5B is a rear perspective view of the patient monitor of FIG. 5A in which a sensor module is connected to the patient monitor in a second orientation.
Figure 5A:
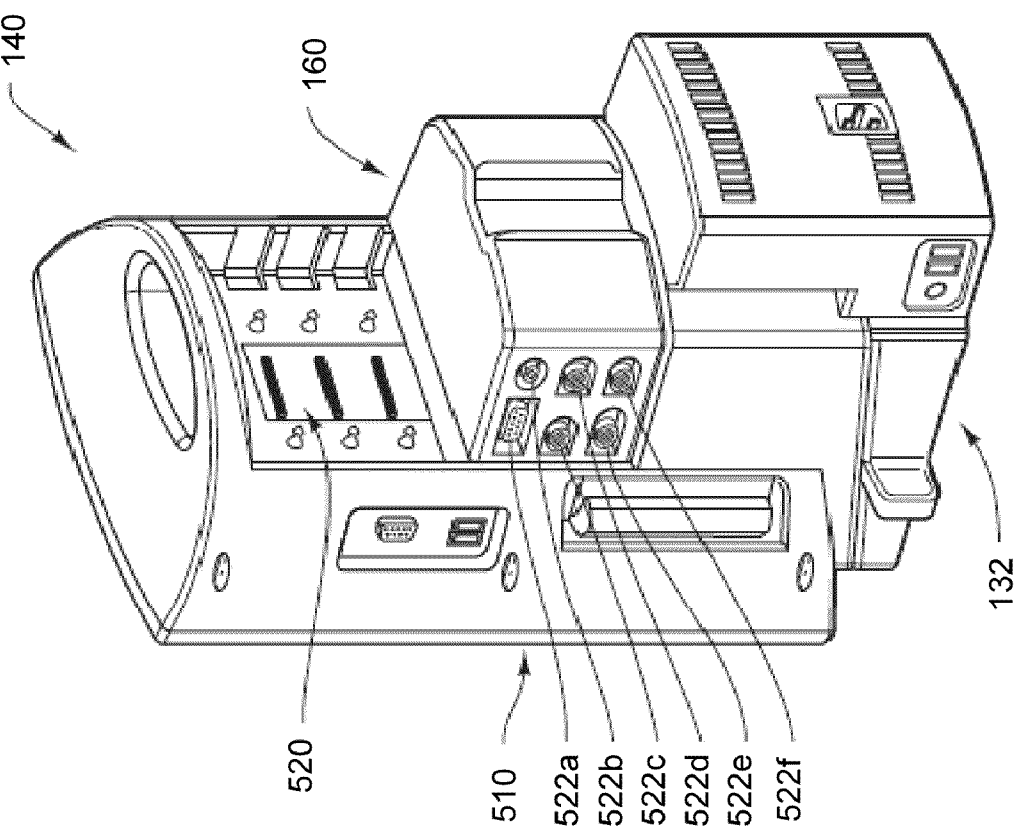
FIG. 5A is a rear perspective view of the patient monitor of FIG. 4 connected to a docking station, and in which a sensor module is connected to a docking region of the patient monitor in a first orientation.

FIG. 5A illustrates an embodiment of a patient monitor 140 connected to a docking station 132, and in which a sensor module 160 is connected to a docking region 520 of the patient monitor 140. Sensor module 160 includes a plurality of connectors or ports 522a, 522b, 522c, 522d, 522e, 522f, which can be configured to couple with one or more wires or cables (not shown). The cables can extend between ports 522 and one or more sensors (not shown), which can be configured to gather data regarding a patient (not shown).

Patient monitor 140 can be configured to be mounted in a substantially fixed position, and sensor module 160 can be configured to transition from a first orientation relative to patient monitor 140 (FIG. 5A) to a second orientation relative to patient monitor 140 (FIG. 5B) without moving patient monitor 140 or docking station 132 from the substantially fixed position. As a result, sensor module 160 can be conveniently manipulated to allow for cables to be run to one side 510 of patient monitor 140 or the other side. In the illustrated embodiment, when sensor module 160 is transitioned from the first orientation to the second orientation, ports 522 are moved from one side 510 of patient monitor 140 to an opposite side of patient monitor 140. Thus, ports 522 are not visible in the view depicted in FIG. 5B.

It will be understood by those having skill in the art that many changes may be made to the details of the above-described embodiments without departing from the underlying principles disclosed herein. The scope of the present invention should, therefore, be determined only by the following claims.

The invention claimed is:

1. A system for locating a medical device comprising:
a device identification subsystem configured to receive a unique identifier associated with a medical device via one of a plurality of network connection points on a network;
a plurality of docking stations, each of the plurality of docking stations associated with one of the plurality of network connection points, wherein the medical device is configured to be selectively coupled with and selectively decoupled from the plurality of docking stations;
a device tracking subsystem configured to associate the unique identifier with the medical device and to track a last known location of the medical device; and
a location subsystem configured to store a location of each of the plurality of network connection points;
wherein the device tracking subsystem identifies the medical device based on the unique device identifier and updates the last known location of the medical device based on the location stored in the location subsystem of the one of the plurality of network connection points used to transmit the unique device identifier and wherein the location subsystem is configured to associate the location of the medical device with the location of the docking station in which the medical device is docked.

2. The system of claim 1, further comprising:
a notification subsystem configured to generate a notification when a specified condition is satisfied.

3. The system of claim 1, further comprising:
a calibration subsystem configured to associate the medical device with calibration information and to evaluate a condition using the calibration information to determine that the medical device requires calibration.

4. The system of claim 1, wherein the device tracking subsystem is further configured to store at least one attribute of the medical device, the at least one attribute selected from the group consisting of calibration information, owner information, expiration information, diagnostic information, and date last used.

5. The system of claim 1, further comprising:
a device querying subsystem configured to query the medical device via the network and to determine that the medical device satisfies a specified criteria.

6. A system for locating a device on a network, the system comprising:
- a network having a plurality of network connection points;
- a medical device comprising:
  - a unique device identifier; and
  - a network interface to transmit the unique device identifier via one of the plurality of network connection points;
- a server comprising:
  - a server network adapter configured to connect to the network;
  - a location subsystem configured to store a location of each of the plurality of network connection points;
  - a device tracking subsystem configured to store a last known device location based on the unique device identifier; and
  - a calibration subsystem configured to associate the medical device with calibration information and to evaluate a condition using the calibration information to determine that the medical device requires calibration;
- wherein the device tracking subsystem identifies the medical device based on the unique device identifier and updates the last known device location based on the location of the one of the plurality of network connection points used to transmit the unique device identifier.

7. The system of claim 6, further comprising:
- a sensor module comprising a unique sensor module identifier;
- wherein the medical device comprises a patient monitor, the patient monitor comprising a sensor module interface configured to connect to the sensor module and to transmit the unique sensor module identifier via the sensor module interface; and
- wherein the device tracking subsystem is further configured to store a last known sensor module location and to update the last known sensor module location based on the location of the one of the plurality of network connection points used to transmit the unique sensor module identifier.

8. The system of claim 7, further comprising:
- a sensor comprising a unique sensor identifier, the sensor configured to connect to the sensor module and configured to transmit the unique sensor identifier the sensor module; and
- wherein the device tracking subsystem is further configured to store a last known sensor location and to update the last known sensor location based on the location of the one of the plurality of network connection points used to transmit the unique sensor identifier.

9. The system of claim 6, wherein the medical device comprises a sensor module.

10. The system of claim 6, wherein the device tracking subsystem is further configured to store at least one attribute of the medical device, the at least one attribute selected from the group consisting of calibration information, owner information, expiration information, diagnostic information, and date last used.

11. The system of claim 6, wherein the server further comprises a notification subsystem configured to generate a notification when a specified condition is satisfied.

12. The system of claim 11, wherein the notification subsystem is further configured to generate a notification that the medical device requires calibration.

13. The system of claim 11, wherein the medical device further comprises a diagnostic unit configured to perform a self-diagnostic test and to communicate a result of the self-diagnostic test to the server; and
- wherein the server further comprises:
  - a diagnostic subsystem configured to evaluate the result of the self-diagnostic test; and
  - wherein the notification subsystem is further configured to generate a notification based on the result of the self-diagnostic test.

14. The system of claim 6, wherein the unique device identifier comprises a media access control (MAC) address associated with the network interface.

15. The system of claim 6, further comprising:
- a radio frequency identification (RFID) transceiver configured to connect to one of the plurality of network connection points; and
- wherein the medical device further comprises an RFID tag configured to transmit the unique device identifier upon interrogation by the RFID transceiver.

16. The system of claim 6, further comprising a plurality of docking stations, each of the plurality of docking stations associated with a respective network connection point; and
- wherein the medical device comprises a portable patient monitor configured to be selectively coupled with and selectively decoupled from the plurality of docking stations; and
- wherein the location subsystem is configured to associate the location of the portable patient monitor with the location of the docking station in which the patient monitor is docked.

17. The system of claim 16, wherein each of the plurality of docking stations comprises:
- a power interface to provide power to the patient monitor while coupled thereto; and
- a network interface to provide communication between the patient monitor and the network server.

18. The system of claim 6, wherein the server further comprises a query subsystem configured to query the medical device via the network and to determine that the medical device satisfies a specified criteria.

19. The system of claim 6, wherein the medical device further comprises:
- a memory configured to store a set of parameters associated with the medical device and to configure the medical device according to the set of parameters.

20. A method for locating a medical device comprising:
- receiving a unique identifier associated with a sensor module at a server via one of a plurality of network connection points on a network;
- determining at the server a location of the network connection point of the sensor module using a location subsystem configured to store a location of each of the plurality of network connection points;
- updating at the server a last known location of the sensor module based on the location of the one of the plurality of network connection points used to transmit the unique identifier;
- transmitting a unique sensor identifier of a sensor to the server via the sensor module, the sensor connected to the sensor module; and
- updating a last known sensor location based on the location of the one of the plurality of network connection points used to transmit the unique sensor identifier.

21. The method of claim 20, further comprising graphically displaying the last known location of one or more of the sensor module and the sensor.

22. The method of claim 20, further comprising storing at least one attribute of the sensor module selected from the group consisting of calibration information, owner information, expiration, diagnostic information, and date last used.

23. The method of claim 20, further comprising generating a notification when a specified condition is satisfied.

24. The method of claim 20, further comprising:
storing calibration information;
associating the calibration information with the sensor module;
evaluating a condition using the calibration information to determine that the sensor module requires calibration; and
generating a notification that the sensor module requires calibration.

25. The method of claim 20, further comprising:
performing a self-diagnostic test at the sensor module;
communicating a result of the self-diagnostic test to the sever;
evaluating the result of the self-diagnostic test; and
generating a notification based on the result of the self-diagnostic test.

26. The method of claim 20, wherein the unique device identifier comprises a media access control (MAC) address associated with the network interface.

27. The method of claim 20, further comprising:
connecting a radio frequency identification (RFID) transceiver to one of the plurality of network connection points; and
applying an RFID tag to the sensor module, the RFID tag configured to transmit the unique device identifier upon interrogation by the RFID transceiver; and
interrogating the RFID tag using the RFID transceiver.

28. The method of claim 20, further comprising:
receiving a query comprising a specified criteria;
querying the sensor module;
determining that the sensor module satisfies the specified criteria.

29. A computer-readable medium comprising program instructions executable on a computer to cause the computer to perform a method for locating a device on a network, the computer-readable medium comprising:
program instructions for receiving a unique identifier associated with a medical device via one of a plurality of network connection points on a network; and
determining a location of the network connection point of the medical device using a location subsystem configured to store a location of each of the plurality of network connection points; and
updating a last known location of the medical device in a device tracking subsystem based on the location of the one of the plurality of network connection points used to transmit the unique identifier; and
graphically displaying the last known location of the medical device.

* * * * *